United States Patent [19]

Hall

[11] 4,324,262

[45] Apr. 13, 1982

[54] ASPIRATING CULTURE CATHETER AND METHOD OF USE

[75] Inventor: John E. Hall, Charlottesville, Va.

[73] Assignee: University of Virginia Alumni Patents Foundation, Charlottesville, Va.

[21] Appl. No.: 551

[22] Filed: Jan. 2, 1979

[51] Int. Cl.³ .......................................... A61B 10/00
[52] U.S. Cl. .................................. 128/756; 128/759; 128/328; 128/349 R; 128/DIG. 9; 128/262
[58] Field of Search ............. 128/3, 262, 269, 207.15, 128/716, 749, 756, 757, 758, 768, 328, 349 R, 349 B, 349 BV, DIG. 9; 239/451

[56] References Cited

U.S. PATENT DOCUMENTS

| | | | |
|---|---|---|---|
| 3,050,066 | 8/1962 | Koean | 128/349 B |
| 3,168,092 | 2/1965 | Silverman | 128/3 |
| 3,502,069 | 3/1970 | Siverman | 128/262 |
| 3,683,908 | 8/1972 | Michael et al. | 128/349 B |
| 3,713,447 | 1/1973 | Adair | 128/347 |
| 3,734,094 | 5/1973 | Calinog | 128/207.15 |
| 3,752,158 | 8/1973 | Kariher | 128/347 |
| 3,766,927 | 10/1973 | Jackson | 128/207.15 |
| 3,796,211 | 3/1974 | Kohl | 128/348 |
| 3,800,781 | 4/1974 | Zalucki | 128/749 |
| 3,830,225 | 8/1974 | Shinnick | 128/756 |
| 3,856,020 | 12/1974 | Kovac | 128/347 |
| 3,867,945 | 2/1975 | Long | 128/349 R |
| 3,894,540 | 7/1975 | Bonner, Jr. | 128/349 R |
| 3,896,815 | 7/1975 | Fettel et al. | 128/349 B |
| 3,938,530 | 2/1976 | Santomieri | 128/349 R |
| 3,941,119 | 3/1976 | Corrales | 128/343 |
| 3,952,747 | 4/1976 | Kimmell, Jr. | 128/303 R |
| 3,981,299 | 9/1976 | Murray | 128/349 B |
| 3,982,544 | 9/1976 | Dyck | 128/349 R |
| 3,985,139 | 10/1976 | Penar | 128/349 B |
| 3,989,571 | 11/1976 | Harautuneian | 128/349 B |
| 3,993,080 | 11/1976 | Loseff | 128/349 B |
| 4,018,231 | 4/1977 | Wallace | 128/349 B |
| 4,023,559 | 5/1977 | Gaskell | 128/269 |
| 4,029,104 | 6/1977 | Kerber | 128/348 |
| 4,243,040 | 1/1981 | Beecher | 128/328 |

FOREIGN PATENT DOCUMENTS

| | | | |
|---|---|---|---|
| 454642 | 7/1928 | Fed. Rep. of Germany | 128/262 |
| 2127125 | 5/1973 | Fed. Rep. of Germany | 128/328 |
| 2805351 | 8/1978 | Fed. Rep. of Germany | 128/328 |
| 955490 | 4/1964 | United Kingdom | 128/349 R |

OTHER PUBLICATIONS

Kalinske et al.; Piag. Usefulness & Safety of Transtracheal Aspiration, N. Engl. J. of Med., vol. 276, Noll 3/16/67 pp. 604–606 submitted by Appl.
Pecora, Method of Determining Bacteria Flora . . . Tract; in the Lancet; 6/8/74, pp. 1149–1151–submitted by Appl.
Bartlett et al.,–Should Fiber Optic Bronchoscopy Aspirates by Cultured; Amer. Rev. of Respiratory Disease, vol. 114, 1976 pp. 73–77 submitted by Appl.

Primary Examiner—Kyle L. Howell
Attorney, Agent, or Firm—Oblon, Fisher, Spivak, McClelland & Maier

[57] ABSTRACT

A catheter adapted to be introduced into a body cavity, such as a bronchial tube or lung, and a method of using the catheter. The catheter consists of inner and outer concentric tubes having a reflected cylindrical membrane attached adjacent their distal ends. Pressurized fluid may be introduced through the perfusate passage running between the tubes and thus between the walls of the reflected membrane in order to provide relative rigidity for the membrane and to seal the reflected end of the membrane, thereby creating a closed pristine chamber, defined by the walls of the reflected membrane about the end of the inner tube. A cage composed of balls mounted on resilient pins may be disposed within the reflected membrane to aid the reflection of the membrane. A portion of the reflected membrane may be perforate. Following introduction of the catheter into a bronchial tube in the method of the invention, the inner tube is extended to open and pass through the reflection, thereby rolling the inner wall about the reflected portion and reversing the inner walls of the pristine chamber. Optionally, a topical antibiotic or local anesthetic may be introduced into the membrane and extruded through the perforations during the introduction or exit, or a lung brush or other sampling means may be inserted through the lumen of the inner tube during use. The catheter may also be used for endotracheal intubation.

18 Claims, 11 Drawing Figures

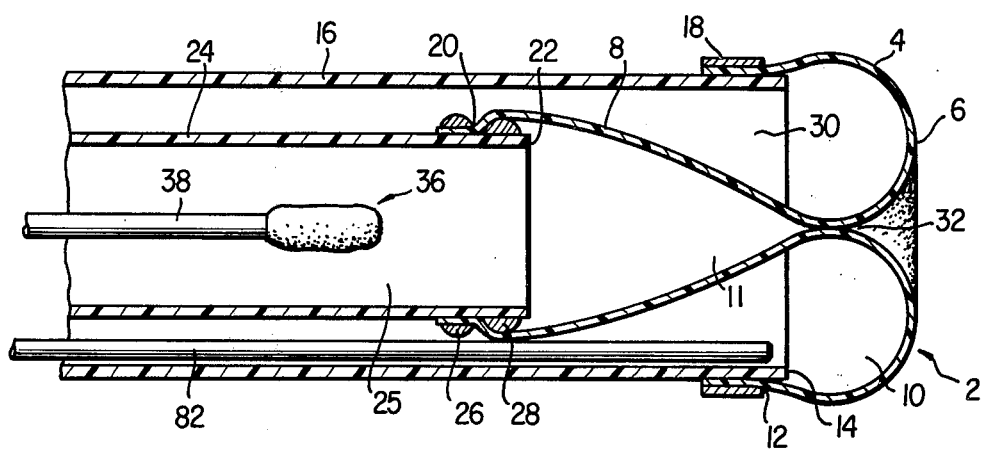
FIG. 1
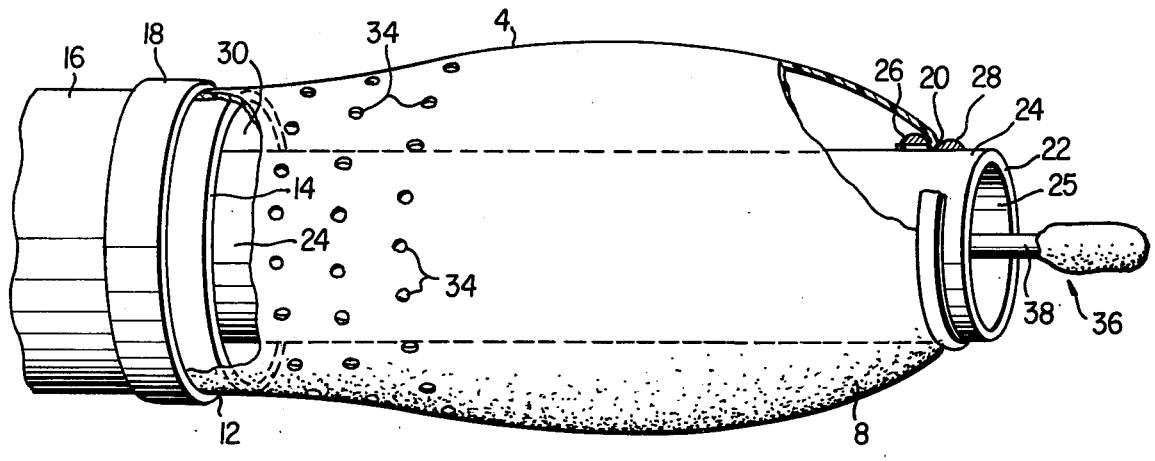
FIG. 3
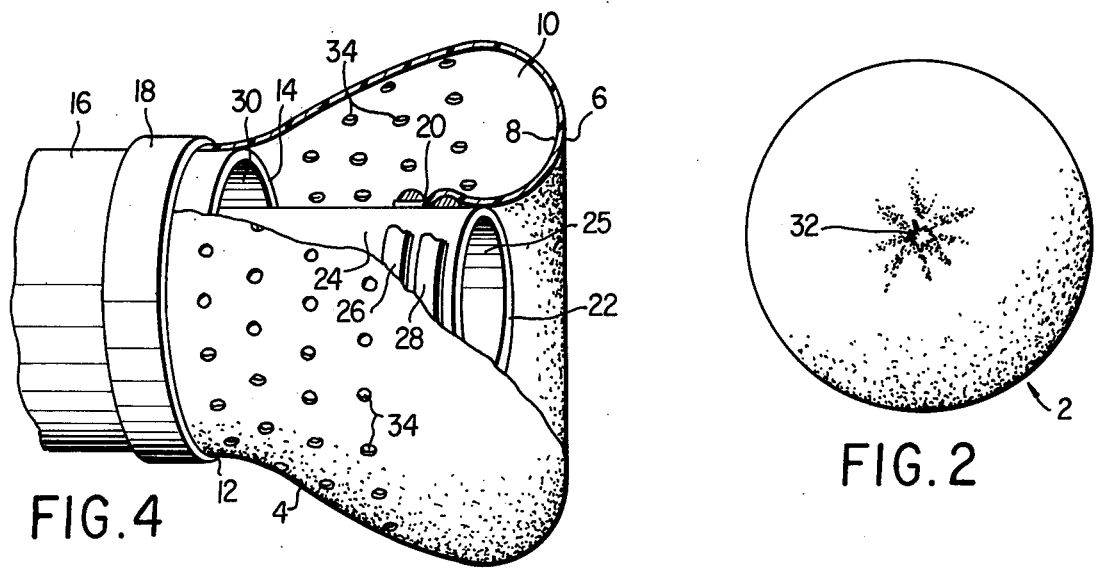
FIG. 4
FIG. 2

ASPIRATING CULTURE CATHETER AND METHOD OF USE

BACKGROUND OF THE INVENTION

1. Field of the Invention

The present invention relates to a catheter for insertion into a body cavity. More particularly, it relates to a catheter for pristine isolation of a portion of a lung or transpharyngeal bronchial tube, and a method for use of the catheter.

2. Description of the Prior Art

Certain medical procedures require the insertion of a catheter into a body cavity for the purpose of examining a portion of the cavity, acquiring a pristine culture or biopsy of cells, introducing a fluid, or aspirating a fluid. Examples of such medical procedures include introducing a catheter into the urinary tract to determine and differentiate kidney infections from bladder or urethral infections, introducing a catheter into the uterus in post partum females to investigate sepsis of the uterus, and introducing a catheter into the tracheobronchial tree to investigate bronchial infections such a pneumonia. However, because the catheter must pass through an entry portion of the body cavity, for example the pharynx or vagina, prior to reaching the portion to be isolated or investigated, and because numerous micro-organisms different from those intended to be studied typically reside in those entry portions, the sterility of the catheter may be compromised and the sampling rendered valueless. Further, and infection may thereby be transmitted from one portion of the cavity to another due to the transit of the contaminated catheter.

When investigating the bronchial tree, a surgical technique known as Transtracheal Aspiration, in which an incision is made which bypasses the pharynx, has been developed in an effort to overcome this problem and attain uncontaminated lung or transpharyngeal bronchial samplings. However, Transtracheal Aspiration is often a dangerous procedure presenting the risks of cutaneous emphysema and hemoptysis, and, as a result, physicians are often hesitant to make use of it.

U.S. Pat. No. 4,023,559 to Gaskell is an example of a catheter designed to be inserted into a body cavity for sampling, irrigating, or draining a portion of the cavity while preventing the contamination of the sampling or drained portion by micro-organisms residing in entry portions of the cavity. The catheter there consists of an outer tube surrounding an inner tube and having a normally closed rounded distal end. The distal end has incisions which open under the pressure resulting from the axial movement of the inner tube. The inner tube remains retracted and the incisions closed as the catheter is passed into a body cavity so that the inner tube may remain sterile while the outer tube is thereby contaminated. When the distal end of the catheter reaches the desired portion of the body cavity, the still sterile inner tube is advanced through the incisions at the rounded distal end of the outer tube so that it may drain or introduce fluid. Optionally a sterile sampling means may be inserted through the lumen of the inner tube. The Gaskell catheter, however, has several shortcomings. First, since the outer tube walls must have sufficient resilient strength to firmly maintain the incisions in a closed condition during entry and exit, the outer tube must therefore be made of a relatively heavy guage tubing. This limits the catheter's flexibility. Secondly, because the outer edges of the incisions are contaminated with extraneous micro-organisms during the transit through the cavity, the previously sterile inner tube also becomes contaminated as it is extended through and contacts the incisions during use. The inner tube is, of course, again contaminated as it is withdrawn past the edges of the incisions after use. As a result, any sampling or culture taken will be contaminated by the inner tube and provide invalid results.

SUMMARY OF THE INVENTION

It is therefore an object of the present invention to provide a catheter capable of isolating a portion of a body cavity in a pristine environment.

It is another object of the present invention to provide a catheter having a sterile or pristine chamber adjacent its distal end.

It is another object of the present invention to provide a catheter capable of extracting a pristine sample from a body cavity.

It is another object of the present invention to provide a catheter capable of converting a pristine space into a protruding pristine tip.

It is another object of the present invention to provide a Transpharyngeal Aspirating Culture Catheter.

It is another object of the present invention to provide a method for isolating a portion of a body cavity in a pristine environment.

It is another object of the present invention to provide a method of acquiring a pristine sample from a body cavity.

It is another object of the present invention to provide a method of transtracheal intubation, aspiration, isolation, and/or culture.

The catheter of the present invention consists essentially of a pair of concentric tubes having a cylindrical perfusate passageway therebetween and a cylindrical membrane made of resilient material and being reflected back upon itself so that each of its ends may be connected adjacent the distal end of one of the tubes, thereby forming a double walled cylindrical chamber at the distal tip of the catheter. When a fluid is introduced through said perfusate passageway and into the space between the walls of the double walled cylindrical chamber formed by the reflected membrane, the membrane becomes relatively rigid and resiliently expands or inflates so as to seal the reflected end of the double walled chamber. Since the interior of the inner wall of the double walled chamber is initially pristine, it thereby forms a closed pristine chamber, or if the inner wall is initially sterile, a closed sterile chamber.

As the catheter is inserted into a body cavity in the method of the invention, the outer wall of the closed, double walled, pristine chamber becomes contaminated by micro-organisms residing in the entry portions of the body cavity but the inner wall remains pristine. As the reflected end of the pristine chamber, which is also the distal tip of the catheter, reaches the desired portion of the body cavity, the inner tube is advanced either manually of by fluid pressure, with respect to the outer tube. The inner tube passes through the reflection and takes the inner wall of the pristine chamber with it until the inner wall is completely reversed and extended behind the distal end of the inner tube, thereby extinguishing the pristine chamber. The respective motions are reversed upon retraction of the inner tube. The inner tube therefore need not come in contact with the contaminated outer wall at any time since the reflection is formed by the pristine inner wall when the inner tube is advancing through it. Further, since most of the resilience and rigidity of the membrane is due to the pressure of the fluid located between the double walls of the membrane, the membrane walls may be made of extremely thin flexible material which readily permits inflation.

Optionally, the outer wall of the pristine chamber defined by the reflected membrane may be perforated to permit perfusate to escape. These perforations should be of such a size and number that the fluid pressure within the reflected membrane is maintained while the outer surface of the reflected membrane is washed by the escaping fluid. The escaping fluid, which is introduced via the perfusate passage may be a local anesthetic, topical antibiotic, or any other fluid desired by the operator. In the case of a topical antibiotic, the outer surface is thereby sterilized to help prevent transmission of micro-organisms.

The apparatus of the invention may further include a sampling means such as a brush or swab located within the lumen of the inner tube. Alternatively, irrigating fluid may be passed through the lumen of the inner tube to wash the cavity, or fluid may be drained therefrom.

A further feature of the apparatus of the invention may be the provision of balls or springs located within the reflected membrane at the point of reflection in order to aid the membrane in retaining its shape and to aid in maintaining the closure of the reflected end of the pristine chamber. The balls or springs may be connected to the outer tube by means of resilient pins or other resilient means to form a cage about the pristine chamber.

In a further embodiment of the apparatus of the invention, the distal end of the outer tube may contain longitudinal slits to facilitate the extension of the inner tube and to increase the flexibility of the inner tube.

In another embodiment of the apparatus of the invention, the inner tube may be eliminated and the end of the reflected membrane connected directly to the sampling brush.

In a preferred embodiment, the catheter comprises a Transpharyngeal Aspirating Culture Catheter which is inserted through the pharynx and into a bronchial tube or lung. In this preferred embodiment it may be used in conjunction with a fiberoptic bronchoscope, in which case it should be of sufficiently small diameter to fit within the passage of the bronchoscope.

The catheter of the preferred embodiment may also include a second membrane on the operator's end of the catheter, the second membrane being a mirror image of the first membrane, and a threaded set pin engagable with an indentation on the inner tube. The operator can therefore judge the extent of extension of the inner tube by examination of the second reflected membrane, and lock it in place by means of the set pin. In the absence of the second membrane, gradations may be provided on the inner tube to gauge the membrane extension.

The catheter of the preferred embodiment could also be used as an endotracheal tube, wherein the inner tube is a breathing tube while the inflated membrane acts to seal the trachea.

The catheter of the present invention may also be used to investigate bleeding in the gastrointestinal tract or in the urinary tract to differentiate bladder infections from kidney infections.

BRIEF DESCRIPTION OF THE DRAWINGS

Various other objects, features and attendant advantages of the present invention will be more fully appreciated as the same becomes better understood from the following detailed description when considered in connection with the accompanying drawings, wherein like reference characters designate like or corresponding parts throughout the several views and wherein:

FIG. 1 is a cross-section of a side view of the reflected membrane of the preferred embodiment;

FIG. 2 is an end view of reflected membrane of FIG. 1;

FIG. 3 is a side view, in partial cross-section, of the reflected membrane of FIG. 1 in a fully extended condition, including the perforations of one of the embodiments;

FIG. 4 is similar to FIG. 3, but shows the inner tube and reflected membrane in a partially extended condition;

DETAILED DESCRIPTION OF THE PREFERRED EMBODIMENTS

Figure 5:
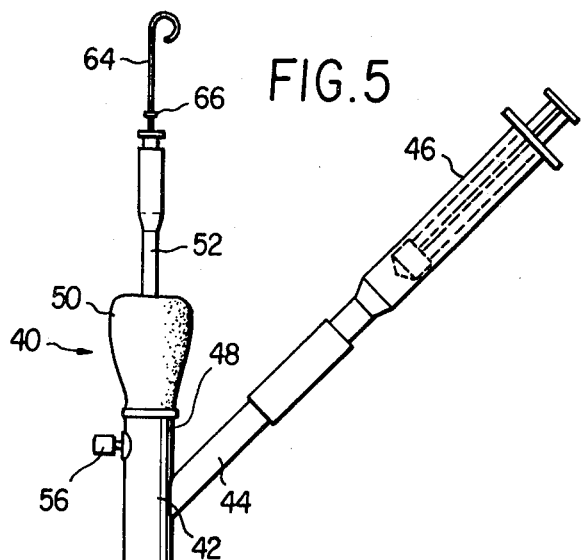
FIG. 5 is a side view of the catheter of FIGS. 1-3.
Figure 6:
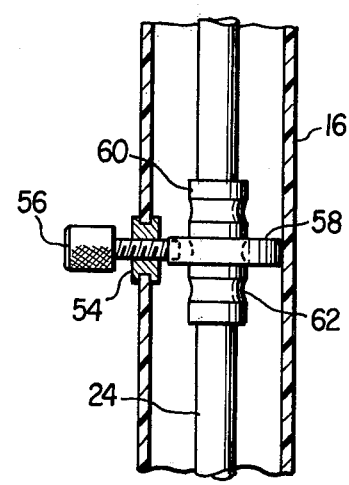
FIG. 6 is a detail of the set pin in FIG. 5.

The preferred embodiments will now be described with reference to the figures.

In FIGS. 1 and 2 the reflected membrane is shown generally at 2. It consists of an outer cylindrical wall 4 which may be reflected back into itself at reflected portion 6 so as to form an inner annular wall 8, thereby resulting in a double walled reflected membrane. An annular perfusate space 10 is formed between the walls, and an annular pristine chamber 11 is formed within the inner wall. The membrane may be made of any thin, strong, and elastic material such as polyurethane or latex. The end 12 of the outer wall of the membrane is connected adjacent the distal end 14, or other convenient portion, of an outer catheter tube 16 by means of a copper band 18 or other fluid tight connecting means such as nylon thread. The end 20 of the inner wall may be connected adjacent the distal end 22 of an inner catheter tube 24 by connecting means such as a pair of threaded, beveled, copper annuli 26 and 28 or other fluid tight connecting means such as nylon thread.

The inner tube 24 extends through the length of the lumen of the outer tube 16 and is axially movable with respect to the outer tube 16. The inner tube 24 has an outer diameter sufficiently smaller than the inner diameter of the outer tube so that a cylindrical perfusate passage 30 may run along the length of the remainder of the lumen. Perfusate under pressure may pass through perfusate passage 30 into perfusate space 10 so as to cause walls 4 and 8 to resiliently stiffen and "balloon". Expansion of the membrane adjacent the reflected end closes off the end of the pristine chamber adjacent the reflection 6 and forms a seal 32. The precise shape of the thus distended membrane is determined by the resilient characteristics of the material from which it is made.

As can be seen in FIGS. 3 and 4, the outer wall of the reflected membrane may contain perforations 34 which permit the perfusate to escape at a controlled rate. The perforations are of such a size and number that adequate pressure is maintained within the perfusate space so that the walls 4 and 8 are still able to "balloon". As may be seen in FIG. 1, the lumen 25 of the inner catheter tube 24 may also contain a sampling means such as lung brush 36 axially movable through the lumen by flexible rod 38.

In the method of operation of the catheter of FIGS. 1 and 2, the catheter is introduced into a body cavity, such as the mouth, and is inserted through the pharynx and into a bronchial tube or lung. This operation may be performed in conjunction with the introduction of a bronchoscope (not shown). Prior to the introduction of the catheter, the distal end 22 of the inner tube 24 is positioned substantially adjacent or within the distal end 14 of the outer tube 16 as seen in FIG. 1. Perfusate under pressure is then introduced through the perfusate passage 30 and into the perfusate space 10 to cause the walls 4 and 8 to "balloon" thereby ensuring the sealing of the pristine chamber at 32.

It can therefore be seen that the pristine chamber and inner tube is sealed and will not be contaminated by micro-organisms residing in the pharynx as the membrane passes therethrough. Further, micro-organisms will not pass into the pristine chamber even if the seal is not complete. This is analogous to Louis Pasteur's swann neck flask experiments which gave evidence to disprove the theory of spontaneous generation; that is, that microbes would not be able to migrate very far down a flask neck. The seal 32, however, acts to further insure that there is no contamination of the pristine chamber; desirable when an anaerobic culture is sought.

Once beyond the pharynx and in a bronchial tube or lung, the pristine chamber 11 and inner catheter tube are exposed by the method shown in FIGS. 3 and 4. In the method, the perfusate is optionally withdrawn and the inner catheter tube 24 is moved forward with respect to the outer tube, towards the reflection 6, as the outer tube is held stationary. As the inner tube moves, it carries the end 20 of the inner wall 8 with it which causes the inner wall to move towards the reflection and to "roll over" at the reflection, as shown in FIG. 4. (If the perfusate has not been withdrawn the rigidity resulting from the pressurized perfusate prevents the inner wall 8 from folding or "crumpling" about the tube 24.) The inner wall therefore reverses itself as it rolls over the point of reflection and becomes part of the outer wall. It may be appreciated that as the inner wall rolls over the point of reflection to become part of the outer wall, it is the inner wall itself which forms the reflection and the length of the pristine chamber 11 is thereby shortened. Beyond a certain extension of the inner tube 24, the seal 32 is broken as the inner tube reaches the point of reflection (as substantially shown in FIG. 4) and the pristine chamber is completely exposed. The inner tube is thereby exposed to the pristine environment of the bronchial area without its ever coming into contact with the edges of the contaminated outer wall 4 since the wall at the reflection has been replaced by the pristine inner wall in the position shown in FIG. 4.

As the inner tube 24 continues to extend beyond the reflection, the membrane eventually becomes fully extended into a cylinder and the reflection and pristine chamber are extinguished, as seen in FIG. 3, which is the working condition of the catheter. It may be appreciated from FIG. 3 that not only has the inner tube 24 been fully extended without contact by the contaminated outer wall 4, but, in the extended position, the contaminated outer wall 4 is removed from the pristine working area of the bronchial tube or lung by the length of inner wall 8, thereby further effectively isolating a portion of the bronchial tube or lung in a pristine environment. Further, if the membrane is then inflated, it may act to seal the portion of the bronchial tree being investigated and even further insure the pristine nature of the culture.

Once the catheter is in the condition shown in FIG. 3, a sampling or culture may be taken (as, for example, by brush 36), or irrigating liquid introduced, or fluid drained, through the lumen 25 of the pristine inner tube 24. When desired, the catheter may be removed by a reversal of the above steps.

In the embodiment having perforations in the outer wall 4, as shown in FIGS. 3 and 4, a fluid such as topical antibiotic, local anesthetic, or other treating fluid may be introduced through the perfusate passage and into the perfusate space of the membrane during entry and exit of the catheter. The use of an anesthetic would lessen any minor discomfort associated with the movement of the catheter and the use of an antibiotic would act to wash and decontaminate the outer wall 4. The operator may, in fact, during insertion or withdrawal, first use one fluid and then, beyond a certain point in the insertion or withdrawal, reverse pressure to withdraw the first fluid, and instead introduce a second fluid.

In FIG. 5, which shows the entire catheter, the operator's end 40 of the outer tube 16 of the catheter includes a Y connection 42. One branch 44 of the Y connection is connected to a hypodermic syringe 46 or other means for introducing perfusate under pressure to the perfusate passage 30. The superior Y branch 48 has attached to the end thereof, a second reflecting membrane 50, which is also connected adjacent the operator's end 52 of the inner tube 24 so as the be a reverse mirror image of the first membrane 2. The superior Y branch 48 also contains an aperature into which a collar 54 for a threaded set pin 56 is inserted. The threaded set pin 56 has attached to it, at the end located within the outer tube 16, a ring 58 which is of a sufficient size to fit around a collar 60 of the inner tube 24. The collar 60 has at least 3 recesses 62 located on its surface which may be engaged by the ring 58 to lock the inner tube in a desired position. As may be seen from FIG. 5, the operator end 64 of the sampling brush rod 38 has gradations 66 marked on its surface to indicate its position within the inner tube.

When performing the method of the invention, the operator may first lock the inner tube in its rest position within the outer tube for insertion through the pharynx, and upon insertion into the bronchial tube, then use the set pin 56 to unlock the inner tube 24 from its rest position. Note that locking the inner tube in its rest position is important in maintaining the sterility of the inner tube 24 because a constant outward pulling force is placed on the inner tube by the resilience of the inflated reflected membrane 2 when the inner tube is in its rest position. The inner tube will therefore initially move slightly foreward as a result of the pulling force when the set pin 56 is released. The operator can then continue to move the inner tube forward while observing the second membrane 50 which is a reverse mirror image of membrane 2, to determine its position with respect to membrane 2. When the inner tube is extended by the desired amount, the operator can use the set pin 56 to again lock it in position and may then extend the sampling brush 36, using gradations 66 to note its position. The inner tube may be extended and retracted either manually or by increasing the fluid pressure within the perfusate space 11. Optionally, the second membrane 50 may be replaced by gradations on the inner tube (not shown) to gauge the extention of the inner tube. Also, the branch 44 of the Y connection may include a membrane (not shown) between the Y connection and the syringe 46. This membrane will expand due to the fluid pressure introduced into membrane 2 and may be used to gauge the fluid pressure.

The catheter may also be used for endotracheal intubation, which is a procedure wherein a tube is inserted into the trachea of a patient in respiratory distress so as to help facilitate respiration. When used for intubation, the inner tube of the catheter would be a breathing tube and constitute an initially sterile airway preventing contamination of the lower trachea. The catheter should then be of such a size that the inner tube 24 could function as a breathing tube and that inflation of the membrane would seal the trachea, thereby keeping contaminants behind the seal and away from the trachea. Culture samplings could also be extracted from the trachea when desired.

Figure 7:
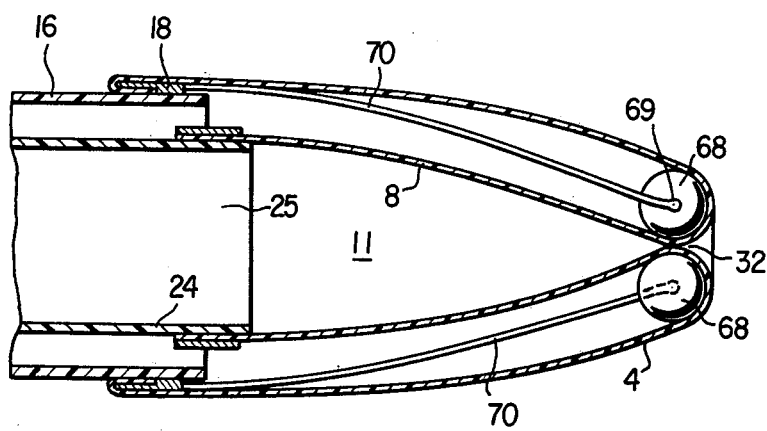
FIG. 7 is a cross-sectional view of a variation of the preferred embodiment.
Figure 8:
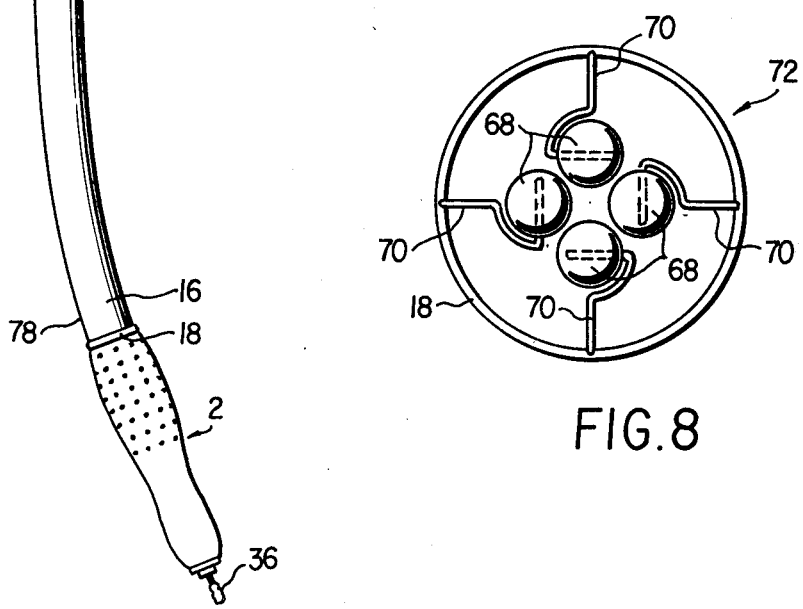
FIG. 8 is an end view of the cage of FIG. 7.

FIGS. 7 and 8 show a further embodiment of the catheter in which a plurality of balls 68 are set within the membrane 2 in an annular array at the point of reflection 6 to aid the membrane in maintaining its shape during insertion. The balls are supported by resilient pins 70 which may be curved and which extend axially within the reflected membrane to the band 18 to which they may be attached, thereby forming a cage 72 about the pristine chamber. The resilient pins tend to urge the balls together to help maintain the seal 32 thereby further insuring the integrity of the pristine chamber 11. The balls may be mounted so as to roll about an axis, such as axis 69 of FIG. 7, as the membrane "rolls" about the reflection during extension or retraction of the inner tube. FIG. 7 shows only one ball as being mounted to permit rolling, however, if this modification is used, all of the balls would be similarly mounted. FIG. 8 shows four balls, however, a lesser or greater number could be used. The balls may also be replaced by springs or other biasing means mounted at the ends of the pins.

The inner and outer tubes may be made of teflon to promote smooth axial movement of the inner tube 24 within the outer tube 16. A lubricant may also be introduced within the perfusate passage for the same purpose.

The catheter may also be used with a fiberoptic bronchoscope, not shown, in which case it should be a sufficiently small diameter to fit within the channel of the bronchoscope. Fiberoptic bronchoscopes are well known to those skilled in the art, and will not be further described.

Figure 9:
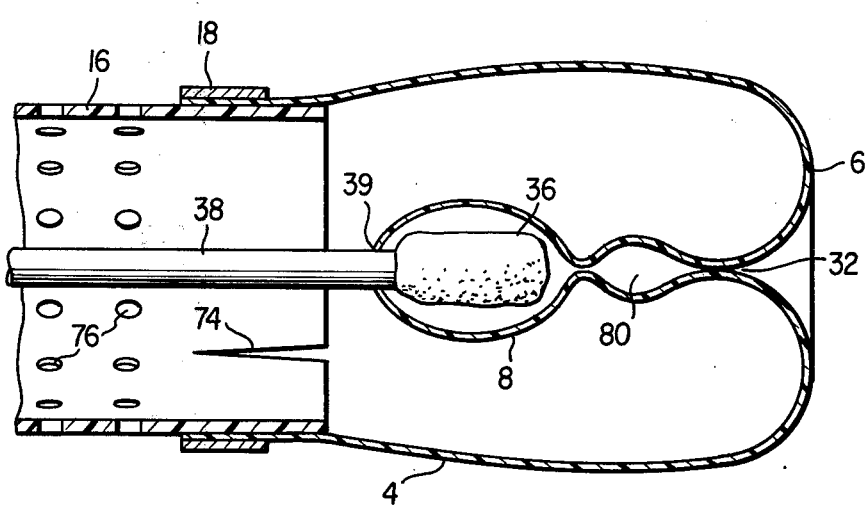
FIG. 9 is a cross-sectional view of another embodiment of the apparatus of the invention.

In another embodiment of the catheter, the inner tube may be completely eliminated and the reflected membrane 2 may be connected between the outer tube 16 and the sampling brush rod 38 at 39, as shown in FIG. 9.

Figure 10:
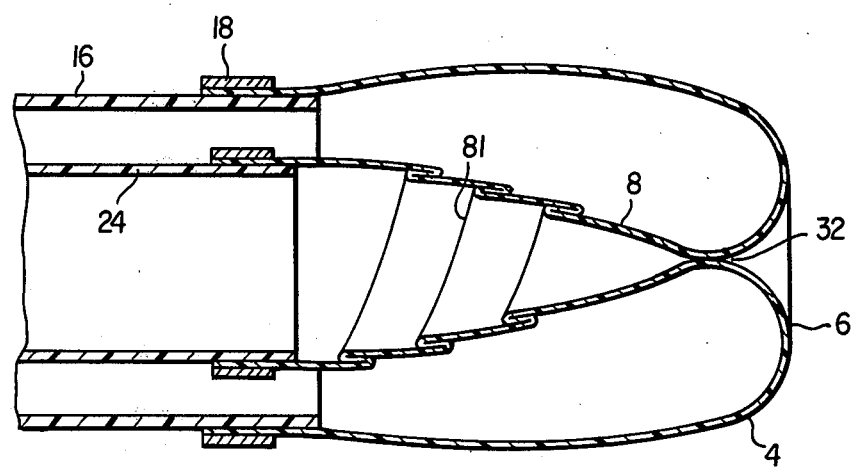
FIG. 10 is a cross-sectional view of yet another embodiment of the invention.

In yet other embodiments: longitudinal slits 74, seen in FIG. 9, may be provided at the distal end of the outer tube 16 to facilitate easier extension of the inner tube and reflection of the membrane and to increase the flexibility of the catheter, particularly in larger catheters. FIG. 9 also shows that the outer tube surface itself may also be, in part, perforate, as at 76. In FIG. 5 it may be seen that the distal end of the catheter may be bent, as at 78, in the manner of a Coude' catheter, to facilitate introduction into the trachea. The inner wall 8 of the membrane may also contain spiral pleats 81, shown in FIG. 10, which cause the membrane to extend when twisted. In the use of this embodiment pressurized fluid is not used, and the pristine chamber 11 is extinguished by advancing the inner tube 24 while rotating it in the sense opposite that of the pleats. Other embodiments can include: shaping the inner wall of the reflected membrane so as to provide several seals along its length, that is, several small balloon portions, as seen at 80 in FIG. 9; and providing one or more guide wires running the length of the catheter to permit additional stiffness and control during insertion, particularly in larger catheters, as can be seen at 82 in FIG. 1.

Figure 11:
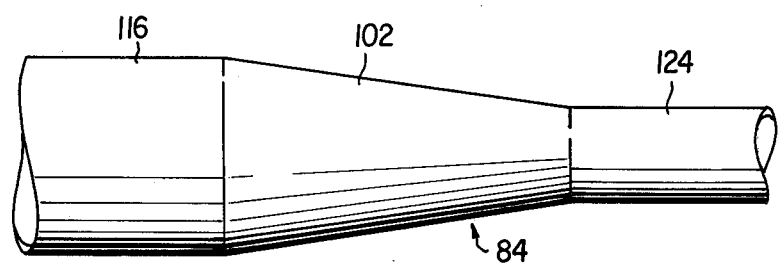
FIG. 11 is a plan view of the catheter manufactured in unitary form, prior to reflecting the inner tube into the outer tube.

As shown in FIG. 11, the inner tube 24, outer tube 16 and membrane 2 may be manufactured as a single tube 84. The tube 84 would have a large diameter end 116 and a small diameter end 124 of approximately equal lengths with a thinner guage intermediate portion 102 connecting the ends 116 and 124. Upon manufacture of the unitary catheter tube 84, one end may be turned "inside out" and reflected back upon itself until the point of reflection reaches the intermediate portion 102. The resulting structure would then be a double walled catheter having walls 116 and 124, with a reflected membrane at one end formed by intermediate portion 102.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A catheter adapted for isolating a portion of a body cavity in a pristine environment, said catheter comprising:

a flexible outer tube having a distal end, said outer tube being adapted for insertion into said body cavity for a substantial portion of said outer tube, whereby said distal end of said outer tube is adjacent said portion of said cavity to be isolated;

an inner tube having a distal end, said inner tube being axially disposed within said outer tube;

means for selectively locking said inner tube relative to said outer tube in at least one position, wherein the distal end of said inner tube is entirely within said outer tube;

a cylindrical reflected membrane having a reflected portion and two ends, one said end of said reflected membrane being connected adjacent said distal end of said inner tube, the other said end of said reflected membrane being connected adjacent said distal end of said outer tube, said reflected membrane defining a pristine chamber, said membrane being shorter in length than said outer tube;

means associated with said membrane for closing said pristine chamber adjacent said reflected portions; and means associated with the other ends of said tubes for introducing fluid under pressure into said reflected membrane.

2. The catheter of claim 1 wherein the outer diameter of said inner tube is smaller than the inner diameter of said outer tube by a finite amount, thereby permitting relative axial movement between said inner and outer tubes and defining a perfusate passage surrounding said inner tube, said perfusate passage constituting said means for introducing said fluid under pressure.

3. The catheter of claim 1 wherein said inner tube has a lumen and a movable sampling means is provided within said lumen of said inner tube.

4. The catheter of claim 3 wherein said sampling means comprises a flexible rod having a brush located at its distal end.

5. A catheter for isolating a portion of a body cavity in a pristine environment, said catheter comprising;
concentric inner and outer tubes having distal ends;
reflected membrane means connected adjacent said distal ends, said reflected membrane means defining a double walled pristine chamber about said distal end of said inner tube;
means associated with said reflected membrane means for closing one end of said pristine chamber; and
at least one spiral pleat located on inner wall of said double walled pristine chamber.

6. A method of isolating a portion of a body cavity in a pristine environment, comprising the steps of:
introducing into an entry portion of said body cavity a catheter defining a closed pristine chamber at one end, said pristine chamber being formed by a double walled reflected membrane having a reflected end wherein the inner wall of said double walls includes at least one spiral pleat;
locating said pristine chamber adjacent said portion of said body cavity to be isolated;
extinguishing said closed pristine chamber by advancing said inner wall through said reflected end while rotating said inner wall in a sense opposite that of said pleat;
isolating said portion of said body cavity;
re-establishing said closed pristine chamber; and
withdrawing said catheter from said body cavity.

7. A method of isolating a portion of a body cavity in a pristine environment, comprising the steps of:
introducing into an entry portion of said body cavity a catheter comprising inner and outer tubes and a reflected membrane connected adjacent the distal ends of said tubes, said reflected membrane being closed adjacent a reflected end to form a closed double walled pristine chamber about said distal end of said inner tube;
introducing fluid under pressure between said double walls;
locating said reflected membrane adjacent said portion of said body cavity to be isolated by simultaneously advancing said inner and outer tubes through said body cavity, whereby said distal ends are adjacent said portion to be isolated;
extinguishing said pristine chamber;
isolating said portion of said body cavity;
re-establishing said pristine chamber; and
withdrawing said catheter from said body cavity by simultaneously moving said inner and outer tubes away from said portion to be isolated.

8. The method of claim 7 wherein said pristine chamber is extinguished by rolling the inner wall of said double wall about said reflected end while advancing said distal end of said inner tube towards said outer tube.

9. The method of claim 7 wherein said pristine chamber is re-established by rolling the inner wall of said double wall about said reflected end while retracting said distal end of said inner tube towards said outer tube.

10. The method of claim 6 or 7 wherein said body cavity is a lung.

11. The method of claim 7 including the step of withdrawing said fluid under pressure prior to extinguishing said pristine chamber 12. The method of claim 7 wherein said portion of said body cavity is isolated by introducing a sampling means through said inner tube.

13. The method of claim 7 wherein said portion of said body cavity is isolated by introducing fluid through said inner tube.

14. The method of claim 7 wherein said portion of said body cavity is isolated by withdrawing fluid through said inner tube.

15. The method of claim 7 wherin the outer wall of said double walled pristine space is perforate and said fluid under pressure is extruded from said perforations.

16. The method of claim 15 wherein said fluid is a treating fluid.

17. The method of claim 7 wherein said body cavity is a trachea and wherein said inner tube includes an inner diameter sufficient for said inner tube to function as a breathing tube.

18. The method of claim 17 including the step of culturing said trachea through said inner tube.

* * * * *